United States Patent [19]
Davis et al.

[11] Patent Number: 6,022,975
[45] Date of Patent: Feb. 8, 2000

[54] PROCESS FOR THE SYNTHESIS OF DIESTERS OF PHOSPHORIC ACID 2,5-DIOXO-4,4-DIPHENYL-IMIDAZOLIDIN-1-YLMETHYL ESTER

[75] Inventors: Edward M. Davis, Zeeland; James E. Ellis, Holland; David A. Katonak, Kentwood, all of Mich.

[73] Assignee: Warner-Lambert Company, Morris Plains, N.J.

[21] Appl. No.: 09/171,259

[22] PCT Filed: Apr. 1, 1997

[86] PCT No.: PCT/US97/05307

§ 371 Date: Oct. 15, 1998

§ 102(e) Date: Oct. 15, 1998

[87] PCT Pub. No.: WO97/41132

PCT Pub. Date: Nov. 6, 1997

Related U.S. Application Data

[60] Provisional application No. 60/016,515, Apr. 30, 1996.

[51] Int. Cl.$^7$ ........................................ C07F 9/06
[52] U.S. Cl. ............................................. 548/112
[58] Field of Search .............................. 548/112

[56] References Cited

U.S. PATENT DOCUMENTS

| | | | |
|---|---|---|---|
| 4,260,769 | 4/1981 | Stella et al. | 548/112 |
| 4,925,860 | 5/1990 | Herbranson et al. | 514/359 |

*Primary Examiner*—Patricia L. Morris
*Attorney, Agent, or Firm*—Merchant & Gould P.C.

[57] ABSTRACT

An improved process for the preparation of a diester of phosphoric acid 2,5-dioxo-4, 4-diphenyl-imidazolidin-1-ylmethyl ester is described where an alkali metal phosphate is treated with a 3-(chloromethyl)- or 3-(bromomethyl)-5,5-diphenyl-2,4-imidazolidinedione to afford the desired product, as well as valuable intermediates used in the process.

7 Claims, No Drawings

PROCESS FOR THE SYNTHESIS OF DIESTERS OF PHOSPHORIC ACID 2,5-DIOXO-4,4-DIPHENYL-IMIDAZOLIDIN-1-YLMETHYL ESTER

CROSS-REFERENCE TO RELATED APPLICATIONS

This application is a 35 U.S.C. 371 application based on PCT/US97/05307 of Apr. 1, 1997, which claims priority to Provisional Application Ser. No. 60/016,515 of Apr. 30, 1996.

BACKGROUND OF THE INVENTION

The present invention relates to an improved process for the production of diesters of phosphoric acid 2,5-dioxo-4,4-diphenyl-imidazolidin-1-ylmethyl ester, which are key intermediates in the preparation of 5,5-diphenyl-[(3-phosphonooxy)methyl]-2,4-imidazolidinedione disodium salt (Cerebyx®, also known as fosphenytoin sodium) described in U.S. Pat. Nos. 4,260,769 and 4,925,860, which are herein incorporated by reference. Cerebyx® is useful as an anticonvulsant, antiepileptic, and antiarrhythmic agent.

A synthetic procedure for preparing 3-(hydroxymethyl)-5,5-diphenylhydantoin dibenzyl phosphate ester is disclosed in Varia S. A., et al., *Journal of Pharmaceutical Sciences*, 1984;73:1068–1073. The aforementioned procedure requires the use of silver dibenzyl phosphate. This reagent is expensive, light sensitive, and silver byproducts are difficult to remove. Thus, special procedures are required to purify the desired product.

Metal salts of dialkyl phosphates have been used for phosphorylation of alkyl halides, and in general, the cation of choice is silver (Sasse K., "Methoden der Organisation Chemis" (Houben-Weyl), Band XLI/2, Thieme Verlag, Stuttgart, 1964:302–306). Precipitation of silver halide from the reaction mixture drives the reaction to completion. Salts of dialkyl phosphates with sodium or potassium as the gegenion have been used with some substrates, but are generally considered to be very poor nucleophiles for reaction with alkyl halides (Khorana H. G., "Some Recent Developments in the Chemistry of Phosphates of Biological Interest," John Wiley & Sons, New York, N.Y., 1961:13–14; Zwierak A, and Kluba M., *Tetrahedron*, 1971;27:3163–3170; U.S. Pat. Nos. 2,494,126, 2,494,283, and 2,494,284). In point of fact, Zwierzak A. and Kluba M., *Tetrahedron*, 1971;27:3163–3170 disclose that sodium or potassium salts of dialkyl phosphates are too unreactive to give satisfactory phosphorylation.

We have surprisingly and unexpectedly found that alkali metal phosphate esters react with either 3-(chloromethyl)- or 3-(bromomethyl)-5,5-diphenyl-2,4-imidazolidinedione to afford diesters of phosphoric acid 2,5-dioxo-4,4-diphenyl-imidazolidin-1-ylmethyl ester. The object of the present invention is an improved, short, efficient, and economical process that can be carried out on a manufacturing scale for the preparation of diesters of phosphoric acid 2,5-dioxo-4,4-diphenyl-imidazolidin-1-ylmethyl ester. Thus, the present process avoids the use of costly and unstable reagents such as silver phosphate esters and associated silver by-products, which are difficult to remove and is amenable to large-scale synthesis.

SUMMARY OF THE INVENTION

Accordingly, a first aspect of the present invention is an improved process for the preparation of a compound of Formula I

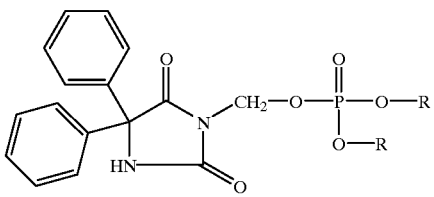

wherein R is aryl,
arylalkyl, or
alkyl;
which comprises treating a compound of Formula II

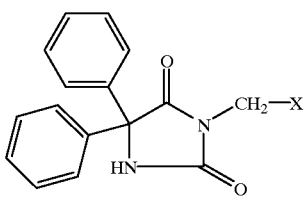

wherein X is chloro or bromo with a compound of Formula III

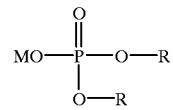

wherein M is an alkali metal, and R is as defined above in a solvent to afford a compound of Formula I.

A second aspect of the present invention is a novel intermediate of Formula I

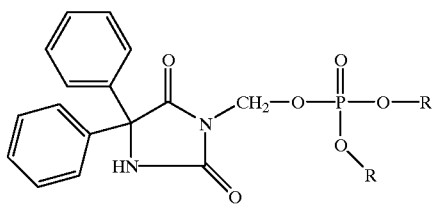

wherein R is aryl,
arylalkyl, or
alkyl with the exclusion of:
phosphoric acid dibenzyl ester 2,5-dioxo-4,4-diphenyl-imidazolidin-1-ylmethyl ester.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group, a naphthyl group, unsubstituted or substituted by 1 to 4 substituents selected from alkyl as defined above, nitro or halogen.

The term "arylalkyl" means an aromatic radical attached to an alkyl radical wherein aryl and alkyl are as defined above, for example, benzyl and the like.

"Halogen" is fluorine, chlorine, bromine, or iodine.

"Alkali metal" is a metal in Group IA of the periodic table and includes, for example, lithium, sodium, potassium, cesium, and the like.

The process of the present invention is a new, improved, economical, and commercially feasible method for preparing compounds of Formula I, which are useful as intermediates in the preparation of fosphenytoin sodium, which is useful as an anticonvulsant, antiepileptic, and antiarrhythmic agent.

The process of the present invention is outlined in the following scheme:

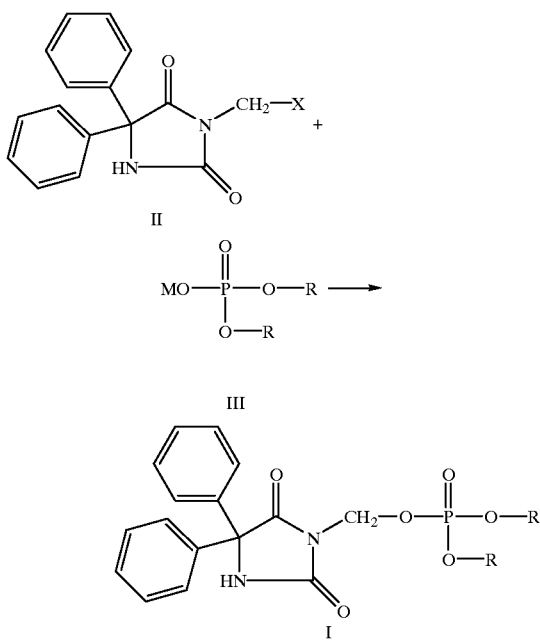

A compound of Formula I wherein R is aryl, arylalkyl, or alkyl is prepared by reacting a compound of Formula II wherein X is chlorine or bromine with a compound of Formula III wherein M is an alkali metal such as, for example, lithium, sodium, potassium, cesium, and the like, and R is as defined above in a solvent such as, for example, acetonitrile and the like at about 25° C. to about the reflux temperature of the solvent for about 1 hour to about 24 hours to afford a compound of Formula I. When M is potassium, optionally a catalytic amount of potassium iodide may be used. When M is sodium, optionally a catalytic amount of tetrabutylammonium iodide or 18-crown-6 may be used. Preferably, the reaction is carried out in acetonitrile at reflux for about 2 hours to about 11 hours.

5,5-Diphenyl-2,4-imidazolidinedione (phenytoin) is readily available or may be prepared according to procedures disclosed in U.S. Pat. No. 2,409,154.

Compounds of Formula III are either known or capable of being prepared by methods known in the art.

The following examples are illustrative to show the present process, the preparation of starting materials, and the use of a compound of Formula I obtained by the present process to prepare 5,5-diphenyl-[(3-phosphonooxy)methyl]-2,4-imidazolidinedione disodium salt useful as an anticonvulsant, antiepileptic, and antiarrhythmic agent.

EXAMPLE 1

Phosphoric Acid Dibenzyl Ester 2,5-Dioxo-4,4-diphenyl-1-imidazolidin-1-ylmethyl Ester Step (A): Preparation of 3-(Chloromethyl)-5,5-diphenyl-2.4-imidazolidinedione A mixture of 250 kg 5,5-diphenyl-2,4-imidazolidinedione (phenytoin), 2.6 kg of potassium carbonate, and 454 L ethyl alcohol is heated to 70° C. to 80° C. One hundred twenty-five kilograms of 37% formaldehyde solution is added, and heating is continued for at least 2 hours. The reaction mixture is cooled slowly, and 600 L of water is added during the cooling cycle. The resulting slurry is cooled to less than 25° C. The product, 3-hydroxymethyl-5,5-diphenyl-2,4-imidazolidinedione, is collected by filtration and washed with water. The wet cake is dried at 20° C. to 50° C. The dried product and 1350 kg of ethyl acetate are charged to a reactor. Five kilograms of dimethyl formamide and 135 kg of thionyl chloride are added at 25° C. to 35° C. The reaction mixture is heated to 35° C. to 60° C. for about 2 hours or until the reaction is essentially complete. The reaction mixture is cooled to 20° C. to 30° C. and combined with 2200 L of aqueous sodium bicarbonate. The organic layer is separated and concentrated by distillation. Heptane is added, and the resulting slurry is cooled. The title compound is collected by filtration and washed with heptane. The wet cake is dried at 20° C. to 50° C. under vacuum to give 3-(chloromethyl)-5,5-diphenyl-2,4-imidazolidinedione, 268 kg (90% yield); mp 161.2–161.8° C.

Step (B): Preparation of Phosphoric Acid Dibenzyl Ester 2,5-dioxo-4,4-diphenyl-imidazolidin-1-ylmethyl Ester Method A A mixture of 250 kg 3-(chloromethyl)-5,5-diphenyl-2,4-imidazolidinedione from Step (A), 270 kg of potassium dibenzyl phosphate, 6 kg of potassium carbonate, 0.75 kg of potassium iodide, and 500 kg of acetonitrile is heated at 70° C. to reflux for 2 to 5 hours or until the reaction is essentially complete. The reaction mixture is cooled to 40° C. to 65° C. and filtered. The solution is stirred with at least 11 kg of activated carbon and filtered using a filter-aid. The reaction solvent is replaced by adding toluene in portions and vacuum distilling. The resulting slurry is cooled to less than 5° C. The title compound is collected by filtration and washed with cold toluene. The wet cake is dried at 50° C. under vacuum to give phosphoric acid dibenzyl ester 2,5-dioxo-4,4-diphenyl-imidazolidin-1-ylmethyl ester, 315 kg (70% yield); mp 118.6–119.7° C.

Method B

Ten grams of 3-(chloromethyl)-5,5-diphenyl-2,4-imidazolidinedione from Step (A), 10.3 g of sodium dibenzyl phosphate, and 0.5 g of sodium carbonate were slurried into 50 mL acetonitrile. The reaction mixture was heated at reflux for 11 hours. The solution was filtered to remove sodium chloride precipitate. The filtrate volume was reduced under vacuum, then 40 mL of toluene added. The solution was seeded and cooled to 0° C. The product was filtered and dried under vacuum at 40° C. 7.38 Grams of the title compound was obtained (43% yield)(product identical with Method A product by high pressure liquid chromatography (HPLC) retention time).

Method C

Ten grams of 3-(chloromethyl)-5,5-diphenyl-2,4-imidazolidinedione from Step (A), 14 g of cesium dibenzyl phosphate, and 0.48 g of cesium carbonate were slurried into 50 mL acetonitrile. The reaction mixture was heated at reflux for 4 hours. The solution was filtered to remove cesium chloride precipitate. The filtrate volume was reduced under vacuum. The solution was seeded and cooled to 0° C. The product was filtered and dried under vacuum at 40° C. 11.5 Grams of the title compound was obtained (63.9% yield) (product identical with Method A product by HPLC retention time).

EXAMPLE 2

Phosphoric Acid 2,5-dioxo-4,4-diphenyl-imidazolidin-1-ylmethyl Ester Dimethyl Ester Thirty grams of 3-(chloromethyl)-5,5-diphenyl-2,4-imidazolidinedione from Step (A), 17.1 g of potassium dimethyl phosphate, 0.6 g of potassium carbonate, and 0.15 g of potassium iodide were slurried into 75 mL of acetonitrile. The reaction mixture was heated at reflux for 3 hours. The solution was filtered to remove potassium chloride precipitate and concentrated to thick oil. Isopropyl alcohol was added to the oil and cooled to 0° C. The product was filtered and dried under vacuum. Sixteen grams of the title compound was obtained (40.9% yield); mp 123.1–124.3° C. Proton nuclear magnetic resonance spectroscopy ($^1$H NMR) deuterated dimethyl sulfoxide (DMSO-$d_6$): 3.6 ppm (d, 6H), 5.3 (d, 2H), 7.3–7.5 (m, 10H), 10.0 (s, 1H); doublets from long range phosphorous coupling.

EXAMPLE 3

Phosphoric Acid Dibutyl Ester 2,5-dioxo-4,4-diphenyl-imidazolidin-1-ylmethyl Ester 23.1 Grams of di(n-butyl)phosphate and 6.2 g of potassium hydroxide were slurried into 100 mL of t-butyl methyl ether. The reaction was stirred until homogeneous and concentrated under vacuum to thick oil of potassium di(n-butyl)phosphate. The oil, along with 30 g of 3-(chloromethyl)-5,5-diphenyl-2,4-imidazolidinedione from Step (A), 0.6 g of potassium carbonate, and 0.15 g of potassium iodide was slurried into 75 mL of acetonitrile. The reaction mixture was heated at reflux for 2.5 hours. The solution was filtered to remove potassium chloride precipitate and then concentrated under vacuum. The residue was crystallized from ethyl acetate/heptane to give 32.8 g of the title compound (69.2% yield); mp 94.8–96.9° C. $^1$H NMR (DMSO-$d_6$): 0.8 ppm (t, 3H), 1.2 (dq, 2H), 1.45 (dt, 2H), 3.85 (dq, 2H), 5.3 (d, 2H), 7.3–7.5 (m, 10H), 9.8 (s, 1H) (peaks at 3.85 and 5.3 doublets from long range phosphorus coupling).

EXAMPLE 4

Phosphoric Acid di-tert-butyl Ester 2,5-dioxo-4,4-diphenyl-imidazolidin-1-ylmethyl Ester 35.5 Grams of 3-(chloromethyl)-5,5-diphenyl-2,4-imidazolidinedione from Step (A), 30.7 g of potassium di(t-butyl) phosphate, 0.6 g of potassium carbonate, and 0.15 g of potassium iodide were slurried into 200 mL acetonitrile. The reaction mixture was heated at reflux for 2.5 hours. The solution was filtered to remove potassium chloride precipitate. The filtrate was cooled to 0° C. and filtered to give 22.3 g of the title compound (38.6% yield); mp 108.5° C. (d). $^1$H NMR (DMSO-$d_6$): 1.3 ppm (s, 18H), 5.2 (d, 2H), 7.3–7.5 (m, 10H), 9.9 (s, 1H); doublet from long range phosphorus coupling.

EXAMPLE 5

5,5-Diphenyl-[(3-phosphonooxy)methyl]-2,4-imidazolidinedione Disodium Salt

A mixture of 250 kg phosphoric acid dibenzyl ester 2,5-dioxo-4,4-diphenyl-imidazolidin-1-ylmethyl ester (Example 1, Step (B)), 9 kg of activated carbon (optionally filter-aid may be added), and 1025 L of acetone is heated at a temperature range of 45° C. to reflux. The activated carbon is removed by filtration. The filtrate is charged to a hydrogenator containing about 6.6 kg of palladium on carbon (50% water wet), and the total water is adjusted to about 28 L. The hydrogenation is run at 20° C. to 40° C. and continued until hydrogen uptake diminishes. The mixture is filtered to remove the catalyst. A minimum of 700 L of water is added, and the solution is concentrated by vacuum distillation at a pot temperature of less than 60° C. The pH of the solution is adjusted to 8.2 to 8.9 with dilute aqueous sodium hydroxide and dilute hydrochloric acid while maintaining a solution temperature of 20° C. to 35° C. At least 27.5 kg of activated carbon is added to the solution. The solution is filtered using a filter-aid. Acetone is added, and the resulting slurry is cooled. The product is collected by filtration, washed with acetone, and dried at 20° C. to 25° C. under vacuum to give the title compound 168 kg (90% yield) on an anhydrous basis. $^1$H NMR deuterated water (D$_2$O): 5.2 ppm (d, 2H), 7.35–7.5 (m, 10H); NH proton exchanged in D$_2$O, doublet from long range phosphorus coupling.

We claim:

1. A process for the preparation of a compound of Formula I

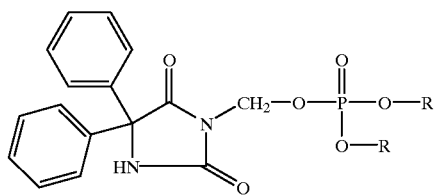

wherein R is aryl,
arylalkyl, or
alkyl;
which comprises reacting a compound of Formula II

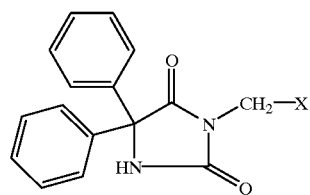

wherein X is chloro or bromo with a compound of Formula III

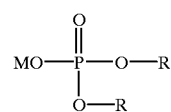

wherein M is an alkali metal, and R is as defined above in a solvent to afford a compound of Formula I.

2. A process according to claim 1 wherein the solvent is acetonitrile.

3. A process according to claim 1 for the preparation of a compound selected from the group consisting of:

Phosphoric acid dibenzyl ester 2,5-dioxo-4,4-diphenyl-imidazolidin-1-ylmethyl ester;

Phosphoric acid 2,5-dioxo-4,4-diphenyl-imidazolidin-1-ylmethyl ester dimethyl ester;

Phosphoric acid dibutyl ester 2,5-dioxo-4,4-diphenyl-imidazolidin-1-ylmethyl ester; and Phosphoric acid di-tert-butyl ester 2,5-dioxo-4,4-diphenyl-imidazolidin-1-ylmethyl ester.

4. A process according to claim 3 for the preparation of phosphoric acid dibenzyl ester 2,5-dioxo-4,4-diphenyl-imidazolidin-1-ylmethyl ester.

5. A process according to claim 1 wherein the compound of Formula II is 3-(chloromethyl)-5,5-diphenyl-2,4-imidazolidinedione.

6. A process according to claim 1 wherein a compound of Formula III is selected from the group consisting of: potassium dibenzyl phosphate: sodium dibenzyl phosphate; cesium dibenzyl phosphate; potassium dimethyl phosphate; sodium dimethyl phosphate; cesium dimethyl phosphate; potassium di(n-butyl) phosphate; sodium di(n-butyl) phosphate; potassium (di(t-butyl) phosphate; sodium di(t-butyl) phosphate; and cesium di(t-butyl) phosphate.

7. A process according to claim 6 wherein the compound of Formula III is potassium dibenzyl phosphate.

* * * * *